United States Patent [19]

Child et al.

[11] Patent Number: 4,927,977
[45] Date of Patent: May 22, 1990

[54] PROCESS AND APPARATUS FOR THE UNIFORM DISTRIBUTION OF A TWO-PHASE FEED IN A CHEMICAL REACTION ZONE

[75] Inventors: Jonathan E. Child, Sewell; Byung C. Choi; Francis P. Ragonese, both of Cherry Hill, all of N.J.

[73] Assignee: Mobil Oil Corporation, New York, N.Y.

[21] Appl. No.: 296,093

[22] Filed: Jan. 12, 1989

[51] Int. Cl.$^5$ .................. C07C 41/05; C07C 24/04
[52] U.S. Cl. .................. 568/695; 568/694; 568/697; 568/698; 568/897
[58] Field of Search .............. 568/694, 695, 697, 698, 568/897

[56] References Cited

U.S. PATENT DOCUMENTS

| | | |
|---|---|---|
| 2,162,913 | 6/1939 | Eversole et al. . |
| 2,477,380 | 7/1949 | Kreps et al. . |
| 2,797,247 | 6/1957 | Keith . |
| 2,798,097 | 7/1957 | Hettinger, Jr. et al. . |
| 2,805,260 | 9/1957 | Keith . |
| 2,830,090 | 4/1958 | Teter et al. . |
| 2,861,045 | 11/1958 | Lauger et al. . |
| 2,891,999 | 6/1959 | Langer, Jr. . |
| 3,006,970 | 10/1961 | Beuther et al. . |
| 3,198,752 | 8/1965 | Bridger et al. . |
| 3,810,849 | 5/1974 | Massle . |
| 3,929,421 | 12/1975 | Werges . |
| 3,989,762 | 11/1976 | Ester . |
| 4,042,633 | 8/1977 | Woods . |
| 4,175,210 | 11/1979 | Selwitz et al. . |
| 4,182,914 | 1/1980 | Imaizumi . |
| 4,214,107 | 7/1980 | Chang et al. . |
| 4,334,890 | 6/1982 | Kochar et al. . |
| 4,418,219 | 11/1983 | Hanes et al. . |
| 4,439,409 | 3/1984 | Puppe et al. . |
| 4,499,313 | 2/1985 | Okumura et al. . |
| 4,605,787 | 8/1986 | Chu et al. . |
| 4,714,787 | 12/1987 | Bell et al. . |
| 4,783,555 | 11/1988 | Atkins . |

FOREIGN PATENT DOCUMENTS 0055045 6/1982 European Pat. Off. .

Primary Examiner—Howard T. Mars
Attorney, Agent, or Firm—Alexander J. McKillop; Charles J. Speciale; Malcolm D. Keen

[57] ABSTRACT

A process and apparatus are provided for the substantially uniform distribution of a two-phase feed in a chemical reaction zone. As applied, for example, to the hydration/etherification of light olefin to alcohol(s) and/or ether(s), the invention results in greater process control and in particular cases, to improved reaction product selectivities.

13 Claims, 1 Drawing Sheet

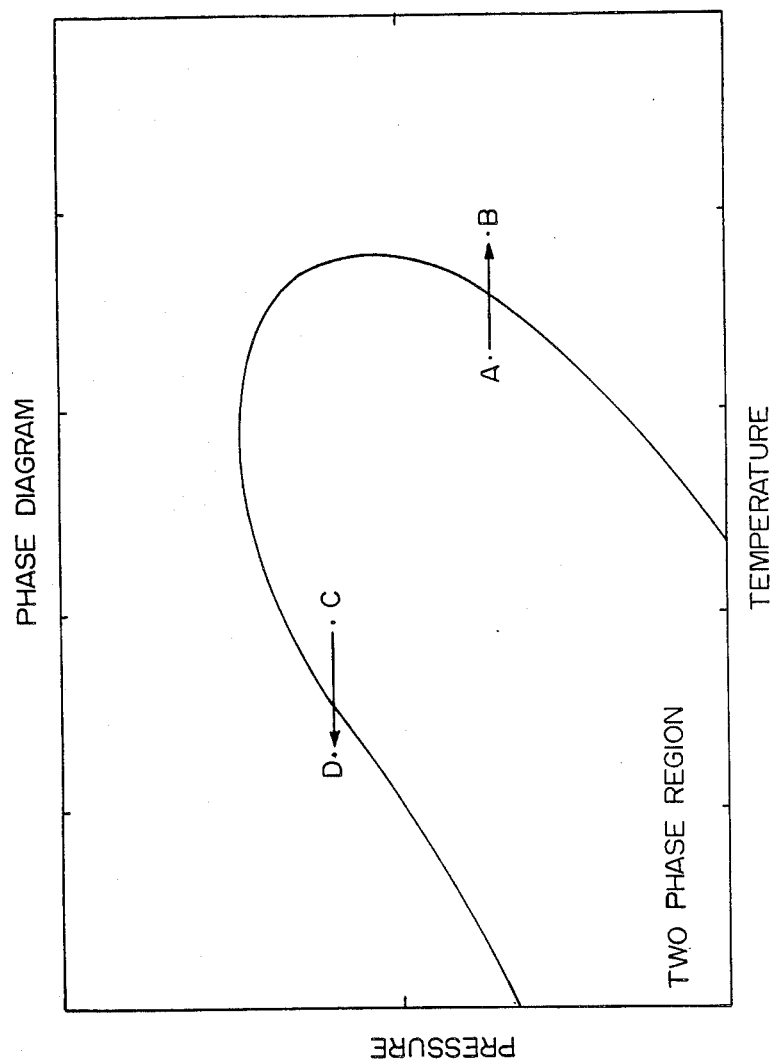
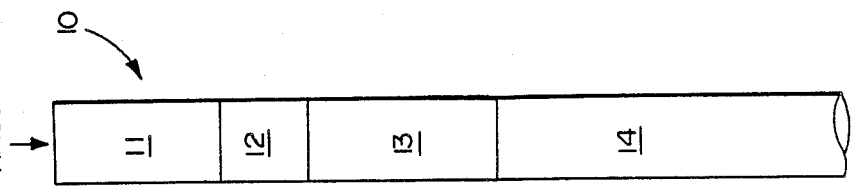

PROCESS AND APPARATUS FOR THE UNIFORM DISTRIBUTION OF A TWO-PHASE FEED IN A CHEMICAL REACTION ZONE

CROSS REFERENCE TO RELATED APPLICATIONS

This application is related by subject matter to commonly assigned, copending U.S. patent application Ser. Nos. 139,543; 139,557; 139,566; 139,567; and, 139,570, each filed Dec. 30, 1987. The contents of these applications, which are concerned with the production of alcohol(s) and/or ether(s), are incorporated by reference herein.

BACKGROUND OF THE INVENTION

This invention relates to a process and apparatus for the uniform distribution of a two-phase feed in an exothermic chemical reaction zone. In one embodiment of the invention, a two-phase feed comprising olefin, water and/or alcohol is substantially uniformly distributed within an olefin hydration/etherification reaction zone wherein the feed undergoes catalytic conversion to alcohols, ethers and their mixtures. The alcohols, ethers and mixtures thereof are useful, inter alia, as high octane blending stocks for gasoline.

It is known that in certain kinds of chemical processes involving the reaction of two liquids or fluids of different densities and limited mutual solubility, when the liquids are mixed to form a two-phase system and are then catalytically reacted under strongly exothermic or endothermic conditions, it becomes desirable and perhaps in some cases, even necessary, to achieve an intermixing between the two liquids before they are subjected to reaction conditions. It has been recognized that it can be particularly difficult to achieve a distribution of one liquid in the other on a uniform basis due to the inherent physical tendency of such liquids to assume different flow rates, even with all other variables being substantially constant. In in effort to solve this problem, U.S. Pat. No. 3,929,421 provides an apparatus and method for continuously and simultaneously mixing, and then catalytically reacting under strongly exothermic or endothermic conditions, two at least partially immiscible fluids of differing density, such fluids being substantially equally distributed across the entrances of each of a plurality of tubular reaction zones. At least one, and preferably both, of the fluids is a liquid and the process conditions employed are preferably liquid phase. The apparatus and method of U.S. Pat. No. 3,929,421 are described with specific reference to the hydration of propylene employing as catalyst, an acidic ion exchange resin or tungsten oxide.

There is a need for an efficient catalytic process to manufacture alcohols and ethers from light olefins thereby augmenting the supply of high octane blending stocks for gasoline. Lower molecular weight alcohols and ethers such as isopropyl alcohol (IPA) and ciisopropyl ether (DIPE) are in the gasoline boiling range and are known to have a high blending octane number. In addition, by-product propylene from which IPA and DIPE can be made is usually available in a fuels refinery. The petrochemicals industry also produces mixtures of light olefin streams in the $C_2$ to $C_7$, molecular weight range and the conversion of such streams or fractions thereof to alcohols and/or ethers can also provide products useful as solvents and as blending stocks for gasoline.

The catalytic hydrarion of olefins to provide alcohol and/or ethers is a well-established art and is of significant commercial importance. Representative olefin hydration processes are disclosed in U.S. Pat. Nos. 2,162,913; 2,477,380; 2,797,247; 3,798,097; 2,805,260; 2,830,090; 2,861,045; 2,891,999; 3,006,970; 3,198,752; 3,810,849; 3,989,762, among others.

Olefin hydration employing zeolite catalysts is known. As disclosed in U.S. Pat. No. 4,214,107, lower olefins, in particular, propylene, are catalytically hydrated over a crystalline aluminosilicate zeolite catalyst having a silica to alumina ratio of at least 12 and a Constraint Index of from 1 to 12, e.g., ZSM-5 type zeolite, to provide the corresponding alcohol, essentially free of ether and hydrocarbon by-product.

According to U.S. Pat. No. 4,499,313, an olefin is hydrated to the corresponding alcohol in the presence of hydrogen-type mordenite or hydrogen-type zeolite Y, each having a silica-alumina molar ratio of from 20 to 500. The use of such a catalyst is said to result in higher yields of alcohol than olefin hydration processes which employ conventional solid acid catalysts. Use of the catalyst is said to offer the advantage over ion-exchange type olefin hydration catalysts of not being restricted by the hydration temperature.

U.S. Pat. No. 4,783,555 describes an olefin hydration process employing a medium pore zeolite as hydration catalyst. Specific catalysts mentioned are Theta-1, said to be preferred, ferrierite, ZSM-22, ZSM-23 and NU-10.

Japanese Laid-Open Patent Application No. 60-246335 discloses the hydration of branched olefins to alcohols in the presence of a zeolite having a silica to alumina ratio of above 10.

The catalyzed reaction of olefins with alcohols to provide ethers is another well known type of process.

As disclosed in U.S. Pat. No. 4,042,633, diisopropyl ether (DIPE) is prepared from isopropyl alcohol (IPA) employing montmorillonite clay catalysts, optionally in the presence of added propylene.

U.S. Pat. No. 4,182,914 discloses the production of DIPE from IPA and propylene in a series of operations employing a strongly acidic cation excnange resin as catalyst.

In U.S. Pat. No. 4,334,890, a mixed $C_4$ stream containing isobutylene is reacted with aqueous ethanol to form a mixture of ethyl tertiary butyl ether (ETBE) and tertiary butyl alcohol (TBA).

U.S. Pat. No. 4,418,219 discloses a process for preparing methyl tertiary butyl ether (MTBE) by reacting isobutylene and methanol in the presence of boron phosphate, blue tungsten oxide or a crystalline aluminosilicate zeolite having a silica to alumina mole ratio of at least 12:1 and a Constraint Index of from 1 to about 12 as catalyst.

As disclosed in U.S. Pat. No. 4,605,787, alkyl tertalkyl ethers such as MTBE and tertiary amyl methyl ether (TAME) are prepared by the reaction of a primary alcohol with an olefin having a double bond on a tertiary carbon atom employing as catalyst an acidic zeolite having a Constraint Index of from about 1 to 12, e.g., ZSM-5, ZSM-11, ZSM-12, ZSM-23 dealuminized zeolite Y and rare earth-changed zeolite Y.

U.S. Pat. No. 4,714,787 discloses the preparation of ethers by the catalytic reaction of linear monoolefins with primary or secondary alcohols employing, as catalyst, a zeolite having a pore size greater than 5 Angstroms, e.g., ZSM-5, zeolite Beta, zeolite X, zeolite Y, etc. Specifically, in connection with the reaction of propylene with methanol to provide methyl isopropyl ether (MIPE), effluent from the reactor is separated into a MIPE fraction, useful as a gasoline blending component, with unreacted propylene, methanol, by-product dimethyl ether (DME) and water at up to one mole per mole of by-product DME, either individually or in combination, being recycled to the reactor.

In European Patent Application No. 55,045, an olefin is reacted with an alcohol to provide an ether, e.g., isobutene and methanol are reacted to provide MTBE, in the presence of an acidic zeolite such as zeolire Beta, ZSM-5, ZSM-8, ZSM-11, ZSM-12, ZSM-23, ZSM-35, ZSM-43 and ZSM-48, and others, as catalysts.

German Patent No. 133,661 describes the reaction of isobutene and methanol to provide a mixture of products including MTBE, butanol and isobutene dimer employing acidic zeolite Y as catalyst.

Japanese Laid-open Patent Application No. 59-25345 describes the reaction of a primary alcohol with a tertiary olefin in the presence of a zeolite having a silica to alumina mole ratio of at least 10 and the X-ray diffraction disclosed therein to provide a tertiary ether.

Apart from U.S. Pat. No. 3,929,421, supra, little attention appears to have been devoted to the manner in which olefin, water and/or alcohol are introduced into an olefin conversion zone to provide alcohols and/or ethers. Known and conventional olefin hydration/etherification processes such as those referred to above describe the introduction of the feed materials into the reactor as a two-phase mixture, e.g., liquid water and/or alcohol and gaseous olefin. As earlier noted, it is difficult to introduce a two-phase reaction mixture into a reactor in a substantially uniform manner and this observation applies fully to a feed containing olefin, water and/or alcohol. Up until the present invention, there has been no recognition or appreciation of the importance of providing substantially uniform distribution of such feed components in an olefin hydration/etherification process.

SUMMARY OF THE INVENTION

It has now been discovered that the manner in which olefin, water and/or alcohol are introduced into a catalytic olefin hydration/etherification zone ("olefin conversion zone") can have a profound effect on the results. Poor or uneven distribution of these feed materials in the olefin conversion zone can lead to poor selectivity and/or runaway process conditions in extreme cases. Unlike two two-phase feeds employed in the prior olefin hydration/etherification processes referred to above which will be unevenly distributed as a result of an imposed pressure drop on the feed, introduction of a single phase feed in accordance with this invention permits substantially uniform distribution of the feed materials in the olefin conversion zone.

It is an object of this invention to provide a process and apparatus for for the substantially uniform distribution of a two-phase reaction mixture, specifically, an at least partially immiscible mixture of at least one liquid component and at least one gaseous component, in an exothermic chemical reaction zone.

It is a particular object of this invention to provide an efficient process for catalytically converting economical, readily available sources of light olefins to alcohol(s), ether(s) or mixtures thereof which are useful as high octane blending stocks for gasoline.

It is another object of the invention to provide a process for the catalytic hydration/etherification of olefin(s) to alcohol(s) and/or ether(s) in an olefin conversion reactor of the tubular type employing acidic zeolite olefin hydration/etherification catalysts and providing substantially uniform distribution of the olefin, water and/or alcohol reactants within each reactor tube.

By way of realizing the foregoing and other objects of the invention, in a process for chemically converting a two-phase feed containing at least one liquid component and at least one gaseous component in the reaction zone of each tube of a tubular reactor to provide one or more reaction products, an improvement is provided which comprises:

(a) adjusting the temperature of the two-phase feed as required to convert said feed into a single liquid or gaseous phase reaction mixture;

(b) substantially uniformly distributing each component of the reaction mixture therein;

(c) readjusting the temperature of the substantially uniform single phase reaction mixture to substantially correspond to the temperature within the reaction zone of a tube; and, (d) introducing temperature-adjusted reaction mixture into the reaction zone of said tube.

As applied to the catalytic hydration/etherification of light olefin(s) to provide alcohol(s) and/or ether(s), the foregoing process and apparatus for carrying out the process result in substantially improved process control by minimizing the opportunity for localized hot spots to develop which could jeopardize efficient operation of the system. In addition, where ether(s) are the primarily desired products, the invention herein provides greater selectivity thereto.

BRIEF DESCRIPTION OF THE DRAWING

FIG. 1 diagrammatically illustrates an apparatus, in the form of a modified reactor tube of an otherwise known type of reactor, of a shell-and-tube type reactor, in accordance with the present invention; and, FIG. 2 represents an idealized phase diagram of a olefin hydration/etherification reaction feed with which the present invention can be practiced.

DESCRIPTION OF THE PREFERRED EMBODIMENTS

While the process and apparatus of the invention are applicable to any exothermic chemical conversion process utilizing a two-phase (liquid and gaseous) feed, it will be particularly described herein in connection with the catalytic hydration/etherification of individual light olefins and mixtures of light olefins of various structures, preferably within the $C_{2-7}$ range, to provide alcohols and/or ethers. Accordingly, the invention is especially applicable to the hydration/etherification of ethylene, propylene, butenes, pentenes, hexenes, heptenes, mixtures of these and other olefins such as gas plant off-gas containing ethylene and propylene, naphtha cracker off-gas containing light olefins, fluidized catalytic cracked (FCC) light gasoline containing pentenes, hexenes and heptenes, refinery FCC propane/propylene streams, etc. For example, a typical FCC light olefin stream possesses the following composition:

| Typical Refinery FCC Light Olefin Composition | | |
| --- | --- | --- |
| | Wt. % | Mole % |
| Ethane | 3.3 | 5.1 |
| Ethylene | 0.7 | 1.2 |
| Propane | 14.5 | 15.3 |
| Propylene | 42.5 | 46.8 |
| Isobutane | 12.9 | 10.3 |
| n-Butane | 3.3 | 2.6 |
| Butenes | 22.1 | 18.3 |
| Pentanes | 0.7 | 0.4 |

The process of the invention is particularly advantageous for the conversion of propylene and propylene-containing streams to mixtures of IPA and DIPE.

When olefin is reacted with water to provide an alcohol, the reaction can be regarded as one of hydration although, of course, some product alcohol can, and does, react with olefin feed to co-produce ether. When olefin is reacting solely with alcohol to provide an ether, the reaction can be regarded as one of etherification. When olefin is reacted with both water and alcohol to provide a mixture of alcohol and ether, the resulting conversion involves both hydration and etherification reactions. In addition, other reactions such as the chemical dehydration of alcohol to ether may occur to some extent.

Lower alcohols which are suitable for reaction with olefin herein, optionally together with water, include alcohols having from 1 to 6 carbon atoms, i.e., methanol, ethanol, propanol, isopropyl alcohol, n-butanol, sec-butanol, tert-butanol, the pentanols and the hexanols.

In accordance with the general requirements of the invention, it is necessary that in the olefin conversion embodiment thereof, the olefin, water and/or alcohol feed components be uniformly distributed within the olefin hydration/etherification zone of the reactor tubes. It should be understood that the composition of the feed need not be identical in each reactor through but that within a given tube, the feed composition will be substantially uniform, at least within the reaction zone thereof. This can be conveniently and effectively accomplished by converting the two-phase feed composition, i.e., an at least partially immiscible mixture of liquid and gaseous component(s), into a single phase composition, i.e., one which is either entirely liquid or entirely gaseous, by effecting a temperature change in the two-phase feed, i.e., either by heating or by cooling the feed to a required extent, followed by effecting the uniform distribution of the components therein.

The choice as between providing a uniform liquid phase feed or a uniform gaseous phase feed well depend in large measure upon the dew points/bubble points of the olefin, water and/or alcohol feed component and their relative amounts in the feed mixture. As shown in FIG. 1 which diagrammatically illustrates a portion of a reactor tube 10 of an otherwise known or conventional shell-and-tube type chemical reactor, in the case of a gaseous propylene and liquid water feed, it is generally advantageous to heat the initial two-phase mixture of these reactants in temperature adjustment zone 11 beyond the dew point of the water thus providing a single gaseous phase in this zone. Following uniform mixing of the propylene gas and water vapor components of the mixture in mixing zone 12, for example, employing an impeller mixer, an in-line static mixer or other suitable mixing device, the feed mixture is readjusted in temperature in temperature adjustment zone 13 to correspond to that of olefin hydration/etherification zone 14 of the reactor tube before introduction the engine. The temperature readjustment within zone 13 can be readily accomplished by, e.g., passing the uniform gaseous mixture of propylene and water vapor through standard column packings to condense the water vapor component of the mixture thereon. The gravity-influenced continued downward movement of the feed mixture, now a substantially uniform propylene gas-liquid water mixture, brings the feed mixture into contact with the olefin hydration/etherification catalyst in zone 14 where conversion of the feed mixture to alcohol and/or ether takes place. When the feed composition is closer to the bubble point of the olefin than the dew point of the water and/or alcohol, it may be preferable to reduce its temperature in temperature adjustment zone 11 below the bubble point of the olefin in order to provide a single liquid phase feed mixture which is then mace homogeneous in mixing zone 12. The now substantially uniform liquid phase is then passed through temperature adjustmenr zone 13 where it is heated to increase its temperature to that of hydration/etherification zone 14 after which it passes into the latter zone. Means for achieving heating/cooling in temperature adjustment zones 11 and 13 are well known in the art and include such devices as electric heaters, heating/cooling jackets, the aforementioned condensation surfaces, and the like.

The operating conditions of the olefin hydration/etherification zone within tube 10 are not especially critical. They include a temperature ranging from ambient up to about 300° C., preferably from about 50° to about 220° C. and more preferably from about 90° to about 200° C., a total system pressure which is sufficient to maintain the water in the liquid state, e.g., at least about 100 psig, preferably at least about 300 psig and most preferably at least about 750 psig and a water to total olefin mole ratio of from about 0.1 to about 30, preferably from about 0.2 to about 15 and most preferably fro about 0.3 to about 5. It may be preferable to operate at low water to total olefin mole ratios as disclosed in U.S. patent application Ser. No. 139,567 referred to above, e.g., at water to total olefin mole ratios of less than about 1.

Reaction times of rrom about 20 minutes to about 20 hours when operating in batcn and a liquid hourly space velocity (LHSV) of from about 0.1 to about 10 when operating continuously are suitable. It is generally preferably to recover any unreacted olefin and recycle it to the reactor.

Those skilled in tne art will recognize that selection of specific operating conditions for a particular olefin feed will influence the nature of rhe hydration/etherification product(s). It will also be appreciated that the precise olefin hydration/etherification conditions selected should, to some extent, reflect the nature of the olefin feed, isoolefins generally requiring milder process conditions than straight chain olefins.

When seeking to maximize the production of ether by the hydration of olefin, the aqueous product effluent from the reactor containing both alcohol and ether reaction products can be introduced into a separator, e.g., a distillation column, for recovery of ether. The dilute aqueous solution of alcohol may be then introduced into a second separator, e.g., another distillation column, where water/alcohol azeotrope is recovered. A fraction of the azeotrope may be fed into dehydration reactor of conventional or otherwise known type and operation to provide a further quantity of ether which can be combined with the ether previously recovered from the olefin hydration reactor. By blending various product streams, almost any ratio of alcohol/ether can be obtained. When alcohol/ether mixtures are to be used as gasoline blending stocks, this capability for adjusting the ratios of alcohol to ether offers great flexibility in meeting the octane requirements for given gasoline compositions. Regulatory considerations aside, alcohol/ether mixtures, e.g., IPA/DIPE mixtures, can constitute up to about 20 weight percent or so of the gasoline to which they are added.

A particularly advantageous procedure for producing mixtures of alcohol and ether, and in particular IPA and DIPE, from the hydration of an olerin-containing feed (a propylene-containing feed in the case of IPA/DIPE mixtures) employing a large pore zeolite such as zeolite Y or zeolite Beta is described in U.S. patent application Ser. No. 139,543 referred to above. In accordance with this procedure as applied, e.g., to the production of IPA/DIPE mixtures, a fresh propane/propylene-containing feed (readily available in many petroleum refineries) and fresh water are cofed, together with recycled unreacted propylene and recycled water from a decanter, into a hydration reactor. The reactor effluent is passed to a separator unit with propane and unconverted propylene being recycled to the reactor, part of the gaseous mixture being purged in order to avoid build-up of propane in the recycle loop. The liquid products from the separator unit are introduced to a distillation unit where an azeotropic mixture of IPA, DIPE, water and propylene oligomers (most $C_6$ olefin) is distilled off and, following cooling, is introduced into a decanter in which phase separation takes place. The upper layer contains mostly DIPE, e.g., 90 weight percent or more, and relatively little water, e.g., 1 weight percent or so. The lower layer is largely water containing negligible quantities of IPA and DIPE. The quantity of the decanter overheads which is recycled can be regulated so as to control the water content in the final product. The bottom fraction of the distillation unit, mainly IPA, is combined with DIPE in the decanter overheads to provide the final IPA/DIPE mixture.

Where it is desire to separate out the alcohol from an alcohol/ether mixture and thus provide essentially pure ether, one can advantageously practice the procedure of U.S. patent application Ser. No. 139,566 referred to above. According to this process as applied to the production of DIPE, the propylene component of a fixed propane/propylene feed undergoes hydration in the presence of a large pore zeolite olefin hydration catalyst, e.g., zeolite Y or zeolite Beta, in a hydration reactor with the effluent therefrom being passed to a separator operating below the olefin hydration reaction temperature. There, two liquid phases form, the aqueous phase being removed and recycled to the hydration reactor. The hydrocarbon-rich phase is flashed to a lower pressure to effect separation of the unreacted $C_3$ components. The flashed product, now containing a substantial amount of IPA product, is introduced to a distillation unit operated at or below atmospheric pressure to effect further purification of the DIPE. The azeotropic IPA, DIPE and water overhead product containing a small amount of propylene oligomer is condensed and thereafter contacted with reactor feed water. The resulting phase separation provides a DIPE product containing at most negligible amounts of IPA and water, e.g., 1.0 weight percent and 0.5 weight percent of these materials, respectively. The remaining aqueous phase can be recycle to the reactor.

While any known or conventional olefin hydration/etherification catalyst can be used in the first stage reaction zone, it is especially advantageous to employ a zeolite which is effective for the catalysis of olefin hydration/etherification to provide alcohols(s) and ether(s). Useful zeolite catalysts include those disclosed in the prior art discussed above as well as in pending U.S. patent application Ser. Nos. 139,557, 139,567 and 139,570 referred to above.

For purposes of this invention, the term "zeolite" is meant to include the class or porotectosilicates, i.e., porous crystalline silicates, which contain silicon and oxygen atoms as the major components. Other components can be present in minor amounts, usually less than 14 mole %, and preferably less than 4 mole %. These components include aluminum, gallium, iron, boon, and the like, with aluminum being preferred. The minor components can be present separately or in mixtures in the catalyst. They can also be present intrinsically in the framework structure of the catalyst.

Representative of the zeolites which are preferred for use herein as olefin hydration/etherification catalysts are zeolite Beta, zeolite X, zeolite L, zeolite Y, ultrastable zeolite Y (USY), dealuminized Y (Deal Y), mordenite, ZSM-3, ZSM-4, ZSM-5, ZSM-12, ZSM-20, ZSM-23, ZSM-38, ZSM-50, MCM-22 and mixtures of any of the foregoing.

Also included within the definition of the useful zeolites are crystalline porous silico-alumino-phosphates such as those disclosed in U.S. Pat. No. 4,440,871, the catalytic behavior of which is similar to that of the aluminosilicate zeolites.

Zeolite Beta is described in U.S. Pat. No. Re. 28,341 (of original U.S. Pat. No. 3,308,069), to which reference is made for details of this catalyst.

Zeolite X is described in U.S. Pat. No. 2,882,244, to which reference is made for the details of this catalyst.

Zeolite L is described in U.S. Pat. No. 3,216,789, to which reference is made for the details of this catalyst.

Zeolite Y is described in U.S. Pat. No. 3,130,007, to which reference is made for details of this catalyst.

Low sodium ultrastable zeolite Y (USY) is described in U.S. Pat. Nos. 3,293,192, 3,354,077, 3,375,065, 3,402,996, 3,449,070 and 3,595,611, to wnich reference is made for details of this catalyst.

Dealuminized zeolite Y (Deal Y) can be prepared by the method found in U.S. Pat. No. 3,442,795, to which reference is made for details of this catalyst.

Zeolite ZSM-3 is described in U.S. Pat. No. 3,415,736, to which reference is made for details of this catalyst.

Zeolite ZSM-5 is described in U.S. Pat. No. Re. 29,948 (of original U.S. Pat. No. 3,702,886), to which reference is made for details of this catalyst.

Zeolite ZSM-12 is described in U.S. Pat. No. 3,832,449, to which reference is made for the details of this catalyst.

Zeolite ZSM-20 is described in U.S. Pat. No. 3,972,983, to which reference is made for the details of this catalyst.

Zeolite ZSM-23 is cescribed in U.S. Pat. No 4,076,842, to which reference is made for the details of this catalyst.

Zeolite ZSM-35 is described in U.S. Pat. No. 4,016,245, to which reference is made for the details of this catalyst Zeolite ZSM-38 is described in U.S. Pat. No. 4,046,859, to which reference is made for the details of this catalyst.

Zeolite ZSM-50 is described in U.S. Pat. No. 4,640,829, to which reference is made for details of this catalyst.

Zeolite MCM-22 and the use of this zeolite to catalyze the reaction of olefin(s) with water to provide alcohol(s), ether(s) or mixtures thereof is disclosed in U.S. patent application Ser. No. 139,55 referred to above.

Zeolite MCM-22, or simply "MCM-22", appears to be related to the composition named "PSH-3" described in U.S. Pat. No. 4,439,409. Zeolite MCM-22 does not appear to contain all the components apparently present in the PSH-3 compositions. Zeolite MCM-22 is not contaminated with other crystal structures, such as ZSM-12 or ZSM-5, and exhibits unusual sorption capacities and unique catalytic utility when compared to the PSH-3 compositions synrhesized in accordance with U.S. Pat. No. 4,439,409.

Zeolite MCM-22 has a composition involving the molar relationship:

$$X_2O_3:(n)YO_2,$$

wherein X is a trivalent element, such as aluminum, boron, iron and/or gallium, preferably aluminum, Y is a tetravalent element such as silicon and/or germanium, preferably silicon, and n is at least about 10, usually from about 10 to about 150, more usually from about 10 to about 60, and even more usually from about 20 to about 40. In the as-synthesized form, zeolite MCM-22 has a formula, on an adhydrous basis and in terms of moles of oxides per n moles or $YO_2$, as follows:

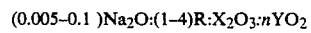

$$(0.005-0.1)Na_2O:(1-4)R:X_2O_3:nYO_2$$

wherein R is an organic component. The Na and R components are associated with the zeolite as a result of their presence during crystallization, and are easily removed by post-crystallization methods hereinafter more parricularly described.

Zeolite MCM-22 is thermally stable and exhibits high surface area (greater than 400 m²/gm as measured [Bruenauer, Emmet and Teller]test) and unusually large sorption capacity when compared to previously described crystal structures having similar X-ray diffraction patterns. As is evident from the above formula, MCM-22 is synthesized nearly free of Na cations. It can, therefore, be used as an olefin hydration/etherification catalyst with acid activity without an exchange step. To the extent desired, however, the original sodium cations of the as-synthesized material can be replaced in accordance with techniques well known in the art, at least in part, by ion exchange with other cations. Preferred replacement cations include metal ions, nydrogen ions, hydrogen precursor, e.g., ammonium, ions and mixtures thereof. Particularly preferred cations are those which tailor the activity of the catalyst for olefin hydration/etherification. These include hydrogen, rare earth metals and metals of Groups IIA, IIIA, IVA, IB, IIB, IIIB, IVB and VIII or the Periodic Table of the Elements.

In its calcined form, zeolite MCM-22 appears to be made up of a single crystal phase with little or no detectable impurity crystal phases and has an X-ray diffraction pattern which is distinguished from the patterns of other known crystalline materials by the lines listed in Table I below:

TABLE I

| Interplanar d-Spacing (A) | Relative Intensity, I/Io × 100 |
|---|---|
| 30.0 ± 2.2 | W-M |
| 22.1 ± 1.3 | W | more specifically by the lines listed in Table II below:

TABLE II

| Interplanar d-Spacing (A) | Relative Intensity, I/Io × 100 |
|---|---|
| 30.0 ± 2.2 | W-M |
| 22.1 ± 1.3 | W |
| 3.91 ± 0.07 | M-VS | and yet more specifically by the lines listed in Table III below:

TABLE III

| Interplanar d-Spacing (A) | Relative Intensity, I/Io × 100 |
|---|---|
| 30.0 ± 2.2 | W-M |
| 22.1 ± 1.3 | W |
| 6.00 ± 0.1 | W-M |
| 4.06 ± 0.07 | W-S |
| 3.91 ± 0.07 | M-VS |

Most specifically, the calcined crystalline material has an X-ray diffraction pattern which includes the lines listed in Table IV beslow:

TABLE IV

| Interplanar d-Spacing (A) | Relative Intensity, I/Io × 100 |
|---|---|
| 30.0 ± 2.2 | W-M |
| 22.1 ± 1.3 | W |
| 12.36 ± 0.2 | M-VS |
| 11.03 ± 0.2 | M-S |
| 8.83 ± 0.14 | M-VS |
| 6.86 ± 0.14 | W-M |
| 6.18 ± 0.12 | M-VS |
| 6.00 ± 0.10 | W-M |
| 5.54 ± 0.10 | W-M |
| 4.92 ± 0.09 | W |
| 4.64 ± 0.08 | W |
| 4.41 ± 0.08 | W-M |
| 4.25 ± 0.08 | W |
| 4.10 ± 0.07 | W-S |
| 4.06 ± 0.07 | W-S |
| 3.91 ± 0.07 | M-VS |
| 3.75 ± 0.06 | W-M |
| 3.56 ± 0.06 | W-M |
| 3.42 ± 0.06 | VS |
| 3.30 ± 0.05 | W-M |
| 3.20 ± 0.05 | W-M |
| 3.14 ± 0.05 | W-M |
| 3.07 ± 0.05 | W |
| 2.99 ± 0.05 | W |
| 2.82 ± 0.05 | W |
| 2.78 ± 0.05 | W |
| 2.68 ± 0.05 | W |
| 2.59 ± 0.05 | W |

These values were determined by standard techniques. The radiation was the K-alpha doublet of copper and a diffractometer equipped with a scintillation counter and an associated computer was used. The peak heights, I, and the positions as a function of 2 theta, where theta is the Bragg angle, were determined using algorithms on the computer associated with the diffractometer. From these, the relative intensities, 100 I/$I_o$, where $I_o$ is the intensity of the strongest line or peak, and d (obs.) the interplanar spacing in Angstroms Units (A), corresponding to the recorded lines, were determined. In Tables I-IV, the relative intensities are given in terms of the symbols W=weak, M=medium, S=strong and VS=very strong. In terms of intensities, these may be generally designated as follows:

|   |   |
|---|---|
| W = | 0-20 |
| M = | 20-40 |
| S = | 40-60 |
| VS = | 60-100 |

It should be understood that these X-ray diffraction patterns are characteristic of all species of the present crystalline composition. The sodium form as well as other cationic forms reveal substantially the same pattern with some minor shifts in interplanar spacing and variation in relative intensity. Other minor variations can occur depending on the Y to X, e.g., silicon to aluminum, mole ratio of the particular sample, as well as its degree of thermal treatment.

Zeolite MCM-22 can be prepared from a reaction mixture containing sources of alkali or alkaline earth metal (M), e.g., sodium or potassium, cation, an oxide of trivalent element X, e.g, aluminum, an oxide of tetravalent element Y, e.g., silicon, an organic (R) directing agent, hereinafter more particularly described, and water, said reaction mixture having a composition, in terms of mole ratios of oxides, within the following ranges:

| Reactants | Useful | Preferred |
|---|---|---|
| $YO_2/X_2O_3$ | 10-80 | 10-60 |
| $H_2O/YO_2$ | 5-100 | 10-50 |
| $OH^-/YO_2$ | 0.01-1.0 | 0.1-0.5 |
| $M/YO_2$ | 0.01-2.0 | 0.1-1.0 |
| $R/YO_2$ | 0.05-1.0 | 0.1-0.5 |

In a preferred method of synthesizing zeolite MCM-22, the $YO_2$ reactant contains a substantial amount of solid $YO_2$, e.g., at least about 30 wt. % solid $YO_2$ Where $YO_2$ is silica, the use of a silica source containing at least about 30 wt. % solid silica, e.g., Ultrasil (a precipitated, spray dried silica containing about 90 wt. % silica) or HiSil (a precipitated hydrated $SiO_2$ containing about 87 wt. % silica, about 6 wt. % free $H_2O$ and about 4.5 wt. % bound $H_2O$ of hydration and having a particle size of about 0.02 micron) favors crystal formation from the above mixture and is a distinct improvement over the synthesis method disclosed in U.S. Pat. No. 4,439,409. If another source of oxide of silicon, e.g., Q-Brand (a sodium silicate comprised of about 28.8 wt. % of $SiO_2$, 8.9 wt. % $Na_2O$ and 62.3 wt. % $H_2O$) is used, crystallization may yield little if any MCM-22 crystalline material and impurity phases of other crystal structures, e.g., ZSM-12, may be produced. Preferably, therefore, the $YO_2$, e.g., silica, source contains at least about 30 wt. % solid $YO_2$, e.g., silica, and more preferably at least about 40 wt. % solid $YO_2$, e.g., silica.

Crystallization of the MCM-22 crystalline material can be carried out at either static or stirred conditions in a suitable reactor vessel such as, e.g., polypropylene jars or teflon-lined or stainless steel autoclaves. The total useful range of temperatures for crystallization is from about 80° C. to about 225° C. for a time sufficient for crystallization to occur at the temperature used, e.g., from about 25 hours to about 60 days. Thereafter, the crystals are separated from the liquid and recovered.

The organic directing agent for use in synthesizing zeolite MCM-22 from the above reaction mixture is hexamethyleneimine which has the following structural formula:

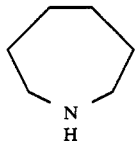

It should be realized that the reaction mixture components can be supplied by more than one source. The reaction mixture can be prepared either batchwise or continuously. Crystal size and crystallization time of the MCM-22 crystalline material will vary with the nature of the reaction mixture employed and the crystalization conditions.

In all cases, synthesis of the MCM-22 crystals is facilitated by the presence of at least about 0.01 percent, preferably about 10 percent and still more preferably about 1 percent, seed crystals based on the total weight of the crystalline product formed.

The MCM-22 crystals can be shaped into a wide variety of particle sizes. Generally speaking, the particles can be in the form of a powder, a granule, or a molded product such as an extrudate having a particle size sufficient to pass through a 2 mesh (Tyler) screen and be substantially retained on a 400 mesh (Tyler) screen. In cases where the catalyst is molded, such as by extrusion, the crystals can be extruded before drying or partially dried and then extruded.

The zeolite olefin hydration/etherification catalysts selected for use herein will generally possess an alpha value of at least about 1. "Alpha value", or "alpha number", is a measure of zeolite acidic functionality and is more fully described together with details of its measurement in *J. Catalysis*, 61, pp. 390-396 (1980). Zeolites of relatively low acidity (e.g., zeolites possessing alpha values of less than about 200) can be prepared by a variety of techniques including (a) synthesizing a zeolite with a high silica/alumina ratio, (b) steaming, (c) steaming followed by dealuminization and (d) substituting framework aluminum with other trivalent metal species. For example, in the case of steaming, the zeolite can be exposed to steam at elevated temperatures ranging from about 500° to about 1200° F. and preferably from about 750° to about 1000° F. This teatment can be accomplished in an atomosphere of 100% steam or an atmosphere consisting of steam and a gas whic is substantially inert to the zeolite. A similar treatment can be accomplished at lower temperatures employing elevated pressure, e.g., at from about 350° to about 700° F. with from about 10 to about 200 atmospheres. Specific details of several steaming procedures may be gained from the disclosures of U.S. Pat. Nos. 4,325,994, 4,374,296 and 4,418,235, the contents of which are incorporated by reference herein. Aside from, or in addition to any of the foregoing procedures, the surface acidity of the zeolite can be eliminated or reduced by treatment with bulky reagents as described in U.S. Pat. No. 4,520,221, the contents of which are incorporated by reference herein.

Prior to their use as olefin hydration/etherification catalysts, the as-synthesized zeolite crystals should be subjected to thermal treatment to remove part or all of any organic consitutent present therein. In addition, the zeolites should be at least partially dried prior to use.

This can be done by heating the crystals to a temperature in the range of from about 200° C. to about 595° C. in an inert atmosphere, such as air, nitrogen, etc. and atmospheric, subatmospheric or superatmospheric pressures for between about 30 minutes to about 48 hours. Dehydration can also be performed at room temperature merely by placing the crystalline material in a vacuum, but a longer time is required to obtain a sufficient amount of dehydration.

The zeolite olefin hydration/etherification catalysts herein, especially in their metal, hydrogen and ammonium forms, can be beneficially converted to other forms by thermal treatment. This thermal treatment is generally performed by heating one of these forms at a temperature of at least about 70° C. for at least 1 minute and generally not longer than 20 hours. While subatmospheric pressure can be employed for the thermal treatment, atmospheric pressure is preferred simply for reasons of convenience. The thermal treatment can be performed at a temperature of up to about 925° C.

The original cations associated with the zeolites utilized herein ca be replaced by a wide variety of other cations according to techniques well known in the art, e.g., by ion-exchange. Typical replacing cations include hydrogen, ammonium, alkyl ammonium and metal cations, and their mixtures. Metal cations can also be introduced into the zeolite. In the case of metal cations, particular preference is given to metals of Groups IB to VIII of the Periodic Table including, by way of example, iron, nickel, cobalt, copper, zinc, platinum, palladium, calcium, chromium, tungsten, molybdenum, rare earth metals, etc. These metals can also be present in the form of their oxides.

A typical ion-exchange technique involves contacting a particular zeolite with a salt of the desired replacing cation. Although a wide variety of salts can be employed, particular preference is given to chlorides, nitrates and sulfates. Representative ion-exchange techniques are disclosed in a number of patents including U.S. Pat. Nos. 3,140,249; 3,140,251 and 3,140,253.

Following contact with a solution of the desired replacing cation, the zeolite is then preferably washed with water and dried at a temperature ranging from about 150° to about 600° F. and thereafter calcined in air or other inert gas at temperatures ranging from about 500° to about 1500° F. for periods of time ranging from about 1 to about 48 hours or more.

It can be advantageous to incorporate the abovedescribed zeolite catalysts into some other material, i.e., a matrix or binder, which is resistant to the temperature and other conditions employed in the first stage reaction zone. Useful matrix materials include both synthetic and naturally-occurring substances, e.g., inorganic materials such as clay, silica and/or metal oxides. Such materials can be either naturally-occurring or can be obtained as gelatinous precipitates or gels including mixtures of silica and metal oxides. Naturally-occurring clays which can be composited with the zeolite include those of the montmorillonite and kaolin families, which families include the sub-bentonites and the kaolins commonly known as Dixie, McNamee-Georgia and Florida clays or others in which the main mineral constituent is haloysite, kaolinite, dickite, nacrite or anauxite. Such clays can be used in the raw state as originally mined or initially subjected to calcination, acid treatment or chemical modification.

In addition to the foregoing materials, the zeolite olefin hydration/etherification catalyst can be composited with a porous metal oxide binder material such as alumina, titania, zirconia, silica, silica-alumina, silica-magnesia, silica-zirconia, silica-thoria, silica-beryllia, silica-titania, etc., as well as ternary oxides compositions such as silica-alumina-thoria, silica-alumina-zirconia, silica-alumina-magnesia, silica-magnesia-zirconia, etc. The binder material can be in the form of a cogel.

In some cases, it may be advantageous to employ as the binder material, one or more essentially non-acidic oxides of metals of Groups IVA and/or IVB of the Periodic Table of the Elements. Particularly useful are the oxides of silicon, germanium, titanium and zirconium with titanium and zirconium being preferred. Combinations of such oxides with other oxides including such relatively acidic oxides as alumina are also useful provided that at least about 40 weight percent, and preferably at least 50 weight percent, of the total metal oxide binder is one or a combination of the aforesaid Group IVA and/or Group IVB metal oxides. Thus, mixtures of oxides which can be used to provide the binder material herein include titania-alumina, titania-magnesia, titania-zirconia, titania-thoria, titania-beryllia, titania-silica-thoria, silica-alumina-zirconia, silica-alumina-magnesia, silica-titania-zirconia, and the like. It may be further advantageous to provide at least part of the Group IVA and/or IVB metal oxide binder, e.g., an amount representing from 1 to 100 weight percent and preferably from about 2 to about 60 weight percent of the total binder material, in colloidal form so as to facilitate the extrusion of the zeolite bound therewith.

The relative proportions of zeolite and metal oxide binder or other matrix material on an anhydrous basis can vary widely with the zeolite content ranging from between about 1 to about 99 weight percent, and more usually in the range of from about 5 to about 90 weight percent, of the dry composite.

Following contact with a solution of the desired replacing cation, the zeolite is then preferably washed with water and dried at a temperature ranging from about 150° to about 600° F. and thereafter calcined in air or other inert gas at temperatures ranging from about 500° to about 1500° F. for periods of time ranging from about 1 to about 48 hours or more.

The following examples are illustrative of the improved olefin hydration process of the present invention.

EXAMPLE 1

The following catalytic hydration/etherification reaction mixture is provided:

| Feed Component | Mole % |
| --- | --- |
| Propylene | 33.2 |
| Propane (Non-reactant) | 14.2 |
| Water | 26.8 |
| Isopropyl Alcohol | 25.8 |

At 1090 psia and 300° F., the foregoing reaction mixture contains a gaseous phase and a liquid phase (41 volume % gaseous phase) and is difficult to uniformly distribute within the tubes of a tubular reactor.

Following cooling of the two-phase reaction mixture, to 290° F. and mechanical mixing, the mixture assumes a substantially uniform single liquid phase. The reduction in temperature corresponds to going from point C to point D on the phase diagram. Following heating of the mixture to 300° F., the substantially uniform mixture is introduced into the reaction zone of each reactor tube where conversion of the feed to isopropyl alcohol and diisopropyl ether occurs.

EXAMPLE 2

At 570 psia and 300° F., the feed mixture of Example 1 is a two-phase mixture containing 95 volume % vapor. Following an increase in the temperature of the mixture to 350° F., the feed is entirely in the vapor phase and is then uniformly agitated to provide a homogeneous mixture of the feed components. This increase in temperature corresponds to going from point A to point B on the phase diagram. Following cooling of the feed mixture to 300° F., the substantially uniform mixture is introduced into the reaction zone of each reactor tube where conversion of the feed to isopropyl alcohol and diisopropyl ether occurs.

EXAMPLE 3

The following catalytic hydration/etherification reaction mixture is provided:

| Feed Component | Mole % |
|---|---|
| Propylene | 13.0 |
| Propane (Non-reactant) | 18.5 |
| Water | 19.8 |
| Isopropyl Alcohol | 33.5 |
| Diisopropyl Ether | 15.2 |

At 880 psia and 350° F., this feed contains liquid and gaseous phases with the latter representing 10 volume % of the total.

Following a reduction of the temperature of the feed to 330° F. and mechanical mixing, the feed assumes a substantially uniform single liquid phase which is reheated to 350° F. just prior to its introduction into the hydration/etherification reaction zon of each reactor tube where conversion of the feed to isopropyl alcohol and diisopropyl ether occurs.

EXAMPLE 4

At 500 psia and 350° F., the feed mixture of Example 3 is a two-phase mixture containing 98.5 volume % vapor. Following an increase in the temperature of the mixture to 400° F., the feed is entirely in the vapor phase which is then mechanically agitated to provide a homogeneous mixture of the feed components. Following cooling of the feed mixture to 350°, the substantially uniform mixture is introduced into the reaction zone of each reactor tube where conversion of the feed to isopropyl alcohol and diisopropyl ether occurs.

What is claimed is:

1. In a process for chemically converting a two-phase feed containing at least one liquid component and at least one gaseous component in the reaction zone of a tube of a tubular reactor to provide one or more reaction products, the improvement which comprises:
    (a) adjusting the temperature of a two-phase feed as required to convert said feed into a single liquid or gaseous phase reaction mixture;
    (b) substantially uniformly distributing each component of the reaction mixture therein;
    (c) readjusting the temperature of the substantially uniform single phase reaction mixture to substantially correspond to the temperature within the reaction zone of a tube; and,
    (d) introducing the temperature-adjusted reaction mixture into the reaction zone of said tube.

2. The process of claim 1 wherein the two-phase feed contains an olefin component, a water component and/or an alcohol component and the reaction zone contains a catalyst which is effective for the conversion of said components to alcohol(s) and/or ether(s).

3. The process of claim 2 wherein the olefin component of the feed contains from two to seven carbon atoms.

4. The process of claim 2 wherein the olefin component contains at least one olefin selected from the group consisting of ethylene, propylene, butenes, pentenes, hexenes, and heptenes.

5. The process of claim 2 wherein the olefin component is an isoolefin.

6. The process of claim 2 wherein the olefin component is isobutylene.

7. The process of claim 2 wherein the alcohol component is selected from the group consisting of methanol, ethanol, n-propanol, isopropyl alcohol, butanols and pentanols.

8. The process of claim 2 wherein the catalyst is an acidic zeolite.

9. The process of claim 8 wherein the zeolite is selected from the group consisting of mordenite, zeolite Beta, USY, X, ZSM-3, ZSM-4, ZSM-5, ZSM-12, ZSM-20, ZSM-23, ZSM-38, ZSM-50 and MCM-22.

10. The process of claim 1 wherein the temperature of the initial two-phase reaction mixture is reduced to provide a single liquid phase reaction mixture, the components of which ar substantially uniformly distributed therein to provide a substantially uniform single liquid phase mixture.

11. The process of claim 10 wherein the temperature of the single liquid phase reaction mixture is increased to reaction temperature prior to introduction into the reaction zone.

12. The process of claim 1 wherein the temperature of the initial two-phase reaction mixture is increased to provide a single gaseous phase reaction mixture, the components of which are substantially uniformly distributed therein to provide a substantially uniform single gaseous phase reaction mixture.

13. The of claim 12 wherein the temperature of the single gaseous phase mixture is decreased to reaction temperature prior to introduction into the reaction zone.

* * * * *